Figure 1:
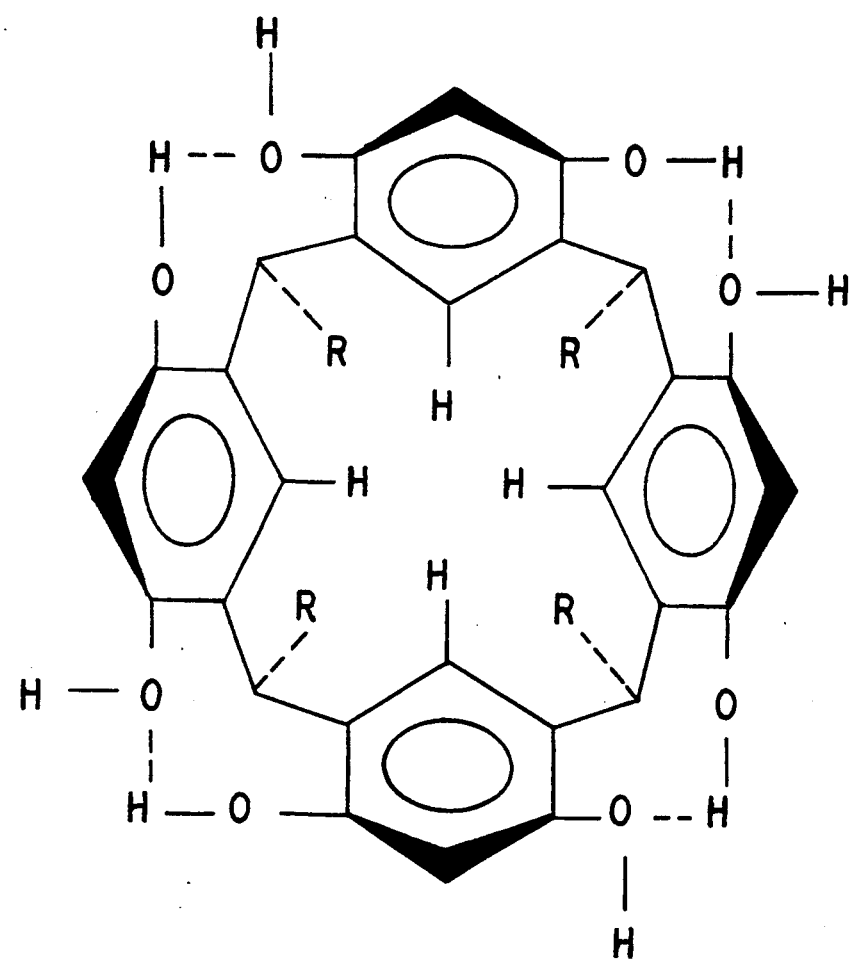

United States Patent [19]
Dalcanale et al.

[11] Patent Number: 5,089,664
[45] Date of Patent: Feb. 18, 1992

[54] PROCESS FOR RECOVERING LACTIC ACID FROM SOLUTIONS WHICH CONTAIN IT

[75] Inventors: Enrico Dalcanale, Pernate; Stefanio Bonsignore, Novara; Annick Du vosel, Caltignaga, all of Italy

[73] Assignee: Istituto Guido Donegani, S.p.A., Novara, Italy

[21] Appl. No.: 452,340

[22] Filed: Dec. 19, 1989

[30] Foreign Application Priority Data

Dec. 22, 1988 [IT] Italy .................. 23057 A/88

[51] Int. Cl.$^5$ ............................................. C07C 51/42
[52] U.S. Cl. .................................................. 562/580
[58] Field of Search ....................................... 562/580

[56] References Cited

U.S. PATENT DOCUMENTS

| 1,906,068 | 4/1933 | Jenemann | 562/580 |
| 2,092,494 | 9/1937 | Bass | 562/580 |
| 3,980,702 | 9/1976 | Grinstead | 562/580 |

FOREIGN PATENT DOCUMENTS 1030727  5/1966  United Kingdom ............... 562/580

Primary Examiner—J. E. Evans
Attorney, Agent, or Firm—Morgan & Finnegan

[57] ABSTRACT

Process for extracting lactic acid from aqueous acidic media is disclosed which process includes treatment with a complexing macrocyclic octol and organic solvent immiscible with water, separating the organic phase containing the lactic acid-macrocyclic octol complex thereby formed, which releases the lactic acid by treatment with alkaline water or with methanol.

7 Claims, 1 Drawing Sheet

PROCESS FOR RECOVERING LACTIC ACID FROM SOLUTIONS WHICH CONTAIN IT

DESCRIPTION OF THE INVENTION

The present invention relates to a process for recovering lactic acid from solutions which contain it.

In particular, the present invention relates to a process for recovering lactic acid from aqueous solutions which contain it, in particular from those solutions which derive from the processing of vegetable products, by means of a system constituted by a complexing agent and an organic extractant selective for lactic acid, which is subsequently liberated and recovered.

So obtained lactic acid constitutes an important product having interesting possibilities of application at an industrial level. In fact, it can be used in the production of dairy products, as an acidulating agent in the alimentary field, as an intermediate for the production of plasticizer agents, adhesives, pharmaceutical products, in the production of lactates, as a mordant in wool dyeing, and so forth.

A particular application field endowed with considerable prospects of industrial development is the field of production of biocompatible and/or biodegradable polymers from lactic acid, useful for manufacturing bags, application films, in the sanitary field, and so on.

These latter applications, which to date can be only accomplished at high costs, can find a cheap and simple alternative in the process according to the instant invention for recovering lactic acid from aqueous solutions which are extremely cheap byproducts from industrial processes e.g., from residual fermentation broths, extracts of vegetable origin, byproducts from the processing of agrarian raw materials, such as the byproducts from corn fermentation treatment, i.e., the so-said "corn-steep liquor", and so forth.

The extraction of lactic acid from such aqueous solutions constitutes a serious problem owing to the extremely high solubility of lactic acid and the presence in the above said aqueous liquids, coming from industrial processes, of a large number of other substances and/or materials of organic and inorganic nature, in amounts exceeding the amount of contained lactic acid.

The extraction of lactic acid from fermentation broths or from aqueous extracts is presently carried out according to several routes. According to the most widely used route, lactic acid is salified in the presence of calcium carbonate, with calcium lactate being obtained. After fermentation residues being filtered, the salt is displaced with sulfuric acid. So obtained lactic acid is further purified by filtration, treatment with activated charcoal and passage over ion-exchange resins, and so forth.

According to another route, calcium lactate is transformed into zinc lactate, which is subsequently purified by means of a plurality of crystallizations in cascade. Lactic acid is subsequently released by means of the addition of hydrogen sulfide.

Also used is the method consisting in the steps of esterification, purification and saponification. More recently, the method was introduced which is based on the neutralization with organic amines, followed by the extraction of the resulting salt with organic solvents.

All of these purification methods are affected by considerable problems of industrial application (corrosion, residual salts, use of ion-exchange resins, etc.), to such an extent that they result to constitute the prevailing contribute to the total product cost.

Therefore, a purpose of the present invention is of providing a simple and cheap process aiming at selectively recovering lactic acid from aqueous solutions, such as fermentation broths and liquors from vegetable origin, such as, e.g., so-said "corn steep liquor", and the like, which is not affected by the above described drawbacks shown by the processes known from the prior art.

Another purpose is of providing a process for recovering lactic acid, by starting from aqueous solutions obtained as processing byproducts, also with a low content of lactic acid and/or containing massive amounts of other components and/or organic and/or inorganic products, without a preliminary concentration thereof.

These purposes are achieved according to the present invention, by means of the use of a system constituted by a complexing agent, selective for lactic acid, dissolved in an extractant solvent selective for the formed complex, as better defined in the following.

Therefore the subject-matter of the instant invention is a process for recovering lactic acid from aqueous media which contain it, which process is characterized in that said aqueous medium is treated with a system consisting of a complexing agent and an organic extractant, selective for lactic acid, which system is constituted by:

a) a complexing agent consisting of at least one macrocyclic octol with crown configuration, with substituents in axial configuration, dissolved in b) at least one organic solvent immiscible with water, selected from among the saturated, optionally halogenated, (cyclo)alkane hydrocarbons, optionally halogenated and/or alkylated aromatic hydrocarbons, and petroleum ether, at a pH value comprised within the range of from 1 to 6, the organic phase constituted by the lactic acid-octol complex dissolved in the organic solvent is separated from the aqueous phase and the organic phase is subsequently treated with water at a pH value comprised within the range of from 7 to 10 or with methanol, with lactic acid being thus liberated, and said lactic acid is then recovered by means of techniques known from the prior art.

More explicitly, within the scope of the instant invention, by means of the definition of "system consisting of a complexing agent and an organic extractant", a system is meant which is constituted by:

a) a complexing agent selective for lactic acid, a macrocyclic octol with crown configuration, with substituents in axial configuration, dissolved in b) an organic vehicle into which the formed lactic acid-octol complex selectively transfers, when the process is carried out at a pH value comprised within the range of from 1 to 6.

In that way, with the preliminary complexation of lactic acid with the octol, a selective extraction into the organic phase of lactic acid dissolved in the aqueous phase used as the starting material is obtained.

Complexed lactic acid is subsequently liberated by means of a treatment with water at a pH value comprised within the range of from 7 to 10 and preferably comprised within the range of from 7 to about 9, with a more or less concentrated aqueous solution of lactic acid being obtained, which can be used as such, or from which concentrated, pure lactic acid can be obtained by means of techniques known from the prior art (concentration, and so forth).

As an alternative, instead of water, methanol can be used, provided that it is not miscible with the organic solvent used; in this case, lactic acid will be liberated as a methanolic solution; and so on.

As the extractant agents, macrocyclic octols are used, which have the general formula (I):

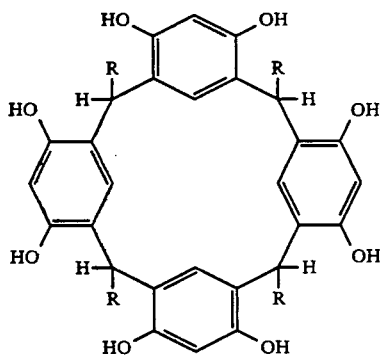

in crown configuration, in which:
the "R" symbols represent linear or branched alkyl radical of from 5 to 18 carbon atoms, in axial configuration.

Among the group of the octols of general formula (I), those are preferred in which "R" is an alkyl radical containing from 6 to 15 carbon atoms, in particular those in which $R = C_6H_{13}$; $C_9H_{19}$; $C_{11}H_{23}$; $C_{15}H_{31}$.

Mixtures thereof can be used.

Said macrocyclic octols are obtained by means of the catalyzed acidic condensation of resorcinol with a suitable alkyl aldehyde, according to as described in J. Org. Chem. 1988, 53, page 5475. According to such a process, the products of general formula (I) can be obtained as one single configurational isomer, denominated "crown isomer", as shown in the hereto attached FIG. 1, in which a perspective view of the molecule is depicted. Only the compounds having a crown configuration, with all of the "R" groups standing in axial position, are used as the extractant agents according to the instant invention.

As above said, in the complexing-extractant system according to the present invention, the macrocyclic octol with axially symmetry of the "R" groups as hereinabove defined [the (a) component of the above defined system] is dissolved in at least one organic solvent medium selective for the complex formed with lactic acid [the (b) component of the system].

The solvents should display the following characteristics. The solvents should be immiscible with water. They should be good solvents for the macrocyclic tetramers of general formula (I). They should not form in their turn preferential bonds (e.g., hydrogen bonds) with the extractant agents of general formula (I).

Within the scope of the above definition, solvents can be used, which are selected from among saturated hydrocarbons, i.e., (cyclo)alkanes, which may also contain halogen substituents, such as hexane, cyclohexane, chloroform, methylene chloride, dichloroethane; aromatic also alkylated and/or halogenated, hydrocarbons, such as benzene, toluene, xylenes, alkylbenzenes, chlorobenzenes; hydrocarbon blends, such as gasoline or kerosene, petroleum ether carbon tetrachloride, and so on; as well as their mixtures.

Particularly advantageous results were obtained with the use of carbon tetrachloride, toluene, benzene and their mixtures.

The process is carried out with strong stirring by operating under pressure and temperature conditions substantially corresponding to room conditions. As already said, the aqueous solution used as the starting material is treated at a pH value comprised within the range of from 1 to 6, and preferably comprised within the range of from 1.4 to 5, with an amount of organic solution which contains the macromolecular octol (I) in a molar excess relatively to the lactic acid contained in said aqueous medium. However, said amount is not binding, and may depend on the solubility of the octol in the solvent, and on similar parameters.

The obtained solution in the organic phase, containing the octol-lactic acid complex, is separated from the aqueous phase by means of known methods (decantation, etc.), and is treated with water at a pH value comprised within the range of from 7 to 10, and preferably comprised within the range of from 7 to 9. As regards the amount, for example, in case the starting solution is constituted by a corn steep liquor, the amount of water or methanol to be used is of about two times as large as the volume of organic solution containing the complex to be treated.

The released acid remains in the aqueous phase, whilst the organic phase, containing all of the macrocyclic octol, is separated from said aqueous phase by decantation, centrifugation, and so forth, and, if so desired, is recycled.

In order to complete the recovery process, times are necessary, which are comprised within the range of from 1 to 12 hours, as a function of the operating conditions of stirring, temperature, and so on.

As above said, the aqueous solutions containing lactic acid are essentially constituted by fermentation broths, aqueous extracts of vegetable origin, the so said "corn steep liquors", and the like, which are available from the market, at a low cost. These are aqueous solutions with a molar titer of lactic acid generally comprised within the range of from 0.06 to about 12.1, besides a large number of other organic and inorganic components.

Nevertheless, the process of the present invention is not bound to a particular minimum or maximum value of such a titer.

Therefore, aqueous solutions can be treated, which have a molar titer of lactic acid comprised within the range of from 0.06 to 12.1 and preferably comprised within the range of from 0.1 to about 3.6.

Therefore, the process can be applied to very diluted solutions of lactic acid (0.5%), as well as to concentrated solutions, practically up to about 90% by weight, without a preliminary concentration or dilution of the solution to be treated being necessary.

The solutions can be submitted to one or more treatment cycles or passes according to the instant invention.

According to a preferred, but non-exclusive, form of practical embodiment, the process of complexation-extraction of lactic acid according to the present invention, in case a corn steep liquor is treated, is carried out by bringing the aqueous phase containing lactic acid into contact, with stirring, at 25° C. for about eight hours, with the organic phase formed by the solvent, selected from the group of the above mentioned solvents, in which the extractant agent of general formula (I) is dissolved in an excess molar ratio. At the interface between the two phases, the selective complexation takes place, followed by the migration of the so-formed complex into the organic phase. The two phases are then separated from each other by decantation or centrifugation. The so-obtained organic phase contains the lactic acid-macrocyclic tetramer (I) complex. Lactic acid is liberated, e.g., by means of a back-extraction with distilled water, according to a volume ratio of 2:1, which cleaves the complex and causes lactic acid to be released; lactic acid migrates into the new aqueous phase; the simultaneously released macroccyclic octol remains in the organic phase.

If so desired, lactic acid can be obtained from the aqueous phase at the desired concentration by evaporation, and so on.

Thanks to its simple and mild operating conditions, the process according to the present invention is particularly advantageous.

EXAMPLES

The present invention is now disclosed in particular by referring to the following examples, which are anyway given for the purpose of merely illustrating the invention without limiting it.

EXAMPLES 1-5

Lactic acid was extracted from aqueous solutions at a known concentration and at a pH value comprised within the range of from 1.4 to 1.9 by means of a $1 \times 10^{-2}$ molar solution of octol 1 (R=$C_{11}H_{23}$) in carbon tetrachloride (see Table 1).

A two-phase mixture (1:4 by volume) of 10 ml of aqueous phase and 40 ml of organic phase is kept vigorously stirred at 25° C. for eight hours. After the complete de-mixing of the two phases from each other, the organic phase is separated and analysed. The quantitative determination of extracted lactic acid is carried out by HPLC analysis of the organic phase, vs. a standard reference solution [conditions: Lichrosorb RP18 column (by Merck); eluent mixture: 73:26:1 $H_2O/CH_3CN/H_3PO_4$-80%; flow rate: 1 ml/minute].

The so obtained organic phase is then extracted once more with distilled water (pH 7). This latter is analysed in its turn via HLPC. The back-extraction in water of lactic acid is carried out as follows: 1 ml of organic phase is mixed with 2 ml of distilled water. After 8 hours of stirring at 25° C., the aqueous phase is centrifuged and analyzed. The results are reported in Table 1.

EXAMPLE 6

By operating in the same way as of Examples 1-5, a 12.10 molar aqueous solution of lactic acid is extracted by means of a $5 \times 10^{-2}$ molar solution of octol 1 in carbon tetrachloride. The results are reported in Table 1.

EXAMPLES 7-11

Lactic acid was extracted from aqueous solutions at a known concentration and at a pH value comprised within the range of from 1.4 to 1.9 by means of a $1 \times 10^{-2}$ molar solution of octol 1 in toluene (see Table 2).

A two-phase mixture (1:1 by volume) of 50 ml of aqueous phase and 50 ml of organic phase is kept vigorously stirred at 25° C. for eight hours. After the complete di-mixing of the two phases from each other, the organic phase is separated and analyzed by acidimetric titration.

The quantitative determination of contained lactic acid is carried out by back-titration of the excess of base which is needed in order to neutralize the solution. A weighed amount of organic solution is titrated with an excess of 0.1N solution of NaOH. The resulting two-phase mixture is kept stirred for 30 minutes and the excess of base is back-titrated with an 0.1N aqueous solution of $H_2SO_4$. The potentiometric line makes it possible the concentration by weight of extracted lactic acid in the toluene phase to be determined with a very high precision. The results are reported in Table 2. The back-extraction with distilled water gave corresponding results.

EXAMPLES 12-16

By operating in the same way as of Examples 7-11, a number of aqueous solutions of lactic acid at a pH comprised within the range of from 1.9 to 2.5 are extracted by means of an $1 \times 10^{-1}$ molar solution of octol 1 in toluene. The results are reported in Table 3. The back-extraction with distilled water gave corresponding results.

EXAMPLES 17-18

By operating in the same way as of Examples 1-5, a 12.10M aqueous solution of lactic acid is respectively extracted with an $1 \times 10^{-2}$ molar solution of octol 1 (R=$C_{11}H_{23}$) and with an $1 \times 10^{-2}$ molar solution of octol 2 (R=$C_6H_{13}$) in benzene. The results are reported in Table 4. The back-extraction with distilled water gave corresponding results.

EXAMPLES 19-20

By operating in the same way as of Examples 1-5, a 12.10M aqueous solution of lactic acid is respectively extracted with an $1 \times 10^{-2}$ molar solution of octols 3 (R=$C_9H_{19}$) and with an $1 \times 10^{-2}$ molar solution of octols 4 (R=$C_{15}H_{31}$) in carbon tetrachloride. The results are reported in Table 4. The back-extraction with distilled water gave corresponding results.

EXAMPLE 21

By operating in the same way as of Examples 1-5, a comparative extraction of a 12.10M aqueous solution of lactic acid is carried out with carbon tetrachloride alone. $0.33 \times 10^{-2}$ mol/liter of lactic acid is extracted.

EXAMPLE 22

By operating in the same way as of Examples 7-11, a comparative extraction of lactic acid from an aqueous solution containing a 12.10 molar concentration thereof is carried out with toluene alone. $1.0 \times 10^{-2}$ mol/liter of lactic acid is extracted.

EXAMPLE 23

Lactic acid was extracted from corn steep liquor (containing about 8-15% by weight of lactic acid) at a pH value of 4.2, by means of a $1 \times 10^{-2}$ molar solution of octol 1 in toluene.

A two-phase mixture (2:1 by volume) containing 50 ml of organic phase and 25 ml of corn steep liquor is kept vigorously stirred at 25° C. for eight hours. After the separation of the two phases, lactic acid is back-extracted from the organic phase with a same volume of distilled water. The concentration of back-extracted lactic acid is determined via HPLC under the same operating conditions as disclosed in Example 1. A value of $5.7 \times 10^{-2}$ mol/liter is obtained, vs. a value of $1 \times 10^{-2}$ mol/liter which was obtained when corn steep liquor was extracted under the same conditions, with toluene alone.

EXAMPLE 24

Lactic acid was extracted from the same corn steep liquor, by means of an $1 \times 10^{-2}$ molar solution of octol 1 in carbon tetrachloride.

By operating in the same way as of Example 23 with a two-phase mixture (4:1 V/V), containing 100 ml of organic phase and 25 ml of corn steep liquor, $5 \times 10^{-2}$ mol/liter of lactic acid are extracted, to be compared to an extracted concentration of $0.55 \times 10^{-2}$ mol/liter only when the extraction is carried out with carbon tetrachloride alone.

TABLE 1

Extraction of lactic acid with octol 1 in CCl$_4$ (Examples 1-6)

| Examples | Concentration (*) of lactic acid (mol/l) in water | Concentration of octol 1 (mol/l) in CCl$_4$ | Concentration (*) of extracted lactic acid (mol/liter) in CCl$_4$ ($\times 10^{-2}$) | Lactic acid % extracted from the aqueous phase ($\times 10^{-2}$) | Molar ratio of extracted lactic acid/octol 1 |
|---|---|---|---|---|---|
| 1 | 1.14 | $10^{-2}$ | 1.7 (1.2) () | 1.5 | 1.7 (1.2) () |
| 2 | 3.57 | | 1.9 (1.3) | 0.53 | 1.9 (1.3) |
| 3 | 6.20 | | 2.1 (1.5) | 0.34 | 2.1 (1.5) |
| 4 | 9.05 | | 3.9 (2.8) | 0.43 | 3.9 (2.8) |
| 5 | 12.10 | | 4.8 (3.5) | 0.40 | 4.8 (3.5) |
| 6 | 12.10 | $5 \times 10^{-2}$ | 16.0 (8.0) | 1.3 | 3.2 (1.6) |

(*) By HPLC.
(**) Measured in the aqueous back-extraction phase.

TABLE 2

Extraction of lactic acid with octol 1 in toluene (Examples 7-11)

| Examples | Concentration (*) of lactic acid (mol/l) in water | Concentration of octol 1 (mol/l) in toluene | Concentration (*) of extracted lactic acid (mol/liter) in toluene ($\times 10^{-2}$) | Lactic acid % extracted from the aqueous phase ($\times 10^{-2}$) | Molar ratio of extracted lactic acid/octol 1 |
|---|---|---|---|---|---|
| 7 | 1.14 | $10^{-2}$ | 0.94 | 0.82 | 0.94 |
| 8 | 3.57 | | 1.16 | 0.32 | 1.16 |
| 9 | 6.20 | | 1.44 | 0.23 | 1.44 |
| 10 | 9.05 | | 1.94 | 0.21 | 1.94 |
| 11 | 12.10 | | 2.30 | 0.18 | 2.30 |

(*) By acidimetric titration.

TABLE 3

Extraction of lactic acid with octol 1 in toluene (Examples 12-16)

| Examples | Concentration (*) of lactic acid (mol/l) in water | Concentration of octol 1 (mol/l) in toluene | Concentration (*) of extracted lactic acid (mol/liter) in toluene ($\times 10^{-2}$) | Lactic acid % extracted from the aqueous phase ($\times 10^{-2}$) | Molar ratio of extracted lactic acid/octol 1 |
|---|---|---|---|---|---|
| 12 | 0.06 | $10^{-1}$ | 0.84 | 14.0 | 0.08 |
| 13 | 0.11 | | 1.06 | 9.6 | 0.11 |
| 14 | 0.22 | | 0.70 | 3.2 | 0.07 |
| 15 | 0.56 | | 1.06 | 1.9 | 0.11 |
| 16 | 1.12 | | 1.36 | 1.2 | 0.14 |

(*) By acidimetric titration.

TABLE 4

Extraction of lactic acid with octols 1, 2, 3, 4 (Examples 17-20)

| Examples | Octol | Chain | Concentration of lactic acid (mol/l) in water | Concentration of octol (mol/l) in organic phase | Concentration (*) of extracted lactic acid (mol/l) in the organic phase (mol/l) ($\times 10^{-2}$) |
|---|---|---|---|---|---|
| 17 | 1 | —C$_{11}$H$_{23}$ | 12.10 | $10^{-2}$ (2) | 4.8 |
| 18 | 2 | —C$_6$H$_{13}$ | | (2) | 3.4 |
| 19 | 3 | —C$_9$H$_{19}$ | | (1) | 3.8 |
| 20 | 4 | —C$_{15}$H$_{31}$ | | (1) | 2.3 |

(1) in CCl$_4$
(2) in C$_6$H$_6$
(*) by HPLC

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

What is claimed is:

1. Process for recovering lactic acid from aqueous media which contain it, which process comprises treating said aqueous medium with a system consisting of a complexing agent and an organic extractant, selective for lactic acid, which system comprises:

a) a complexing agent consisting of at least one macrocyclic octol, the macrocyclic octol has the formula (I):

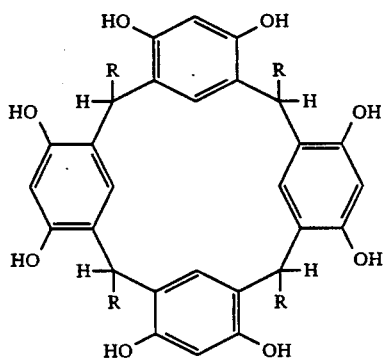

in crown configuration, in which:

the "R" symbols represent linear or branched alkyl radical of from 5 to 18 carbon atoms, in axial configuration dissolved in b) at least one organic solvent immiscible with water, selected from among alkanes, halogenated alkanes, cycloalkanes and halogenated cycloalkanes, aromatic hydrocarbons, halogenated and/or alkylated aromatic hrdrocarbons and hydrocarbon blends at a pH value within the range of from 1 to 6, the organic phase constituted by the lactic acid-octol complex dissolved in the organic solvent is separated from the aqueous phase and the organic phase is subsequently treated with water at a pH value within the range of from 7 to 10 or with methanol, with lactic acid being thus liberated, and said lactic acid is then recovered.

2. Process according to claim 1, wherein in the macrocyclic octol of formula (I) the "R" symbols represent alkyl radicals containing from 6 to 15 carbon atoms; and their mixtures.

3. Process according to claim 1, wherein the organic solvent immiscible with water is selected from among hexane, cyclohexane, chloroform, methylene chloride, dichloroethane, xylenes, alkylbenzenes, chlorobenzenes, gasoline, kerosene and petroleum ether and their mixtures.

4. Process according to claim 1, wherein the aqueous medium which contains lactic acid is treated with the system formed by the organic solvent containing the macromolecular octol (I) in a molar excess relatively to the lactic acid contained in said aqueous medium.

5. Process according to claim 1, wherein the aromatic hydrocarbon is halogenated and/or alkylated.

6. Process according to claim 2, wherein the "R" symbols are selected from among the group consisting of $C_6H_{13}$, $C_9H_{19}$, $C_{11}H_{23}$, and $C_{15}H_{31}$ and their mixtures.

7. Process according to claim 1, wherein the organic solvent is selected from among carbon tetrachloride, benzene and toluene and their mixture.

* * * * *